United States Patent [19]

Abe et al.

[11] Patent Number: 4,993,825
[45] Date of Patent: Feb. 19, 1991

[54] DEVICE FOR PHOTOGRAPHING EYE MOVEMENT

[75] Inventors: Kuniomi Abe, Kobe; Tatsuya Kasahara, Amagasaki, both of Japan

[73] Assignee: Konan Camera Research Institute Inc., Hyogo, Japan

[21] Appl. No.: 442,137

[22] Filed: Nov. 28, 1989

[30] Foreign Application Priority Data

Nov. 29, 1988 [JP] Japan ................................ 63-303332

[51] Int. Cl.⁵ ............................................. A61B 3/14
[52] U.S. Cl. ................................... 351/210; 351/209; 351/206
[58] Field of Search ................ 351/206, 209, 210, 212

[56] References Cited

U.S. PATENT DOCUMENTS 3,827,789 8/1974 Molner et al. ........................ 351/210
4,648,052 3/1987 Friedman et al. .................. 351/210

Primary Examiner—Paul M. Dzierzynski
Attorney, Agent, or Firm—Koda and Androlia

[57] ABSTRACT

A device for photographing eye movement including a target comprising a plurality of lights arranged in a cross-shape with the center thereof being positioned on the eye axis of an examinee, a TV camera positioned behind the target so that at least a principal point of the TV camera's lens thereof is located on an optical line that passes near the center of the target and the examinee's pupil and a light receiving element set on the optical line so that an eye image is formed on the light receiving element.

6 Claims, 4 Drawing Sheets

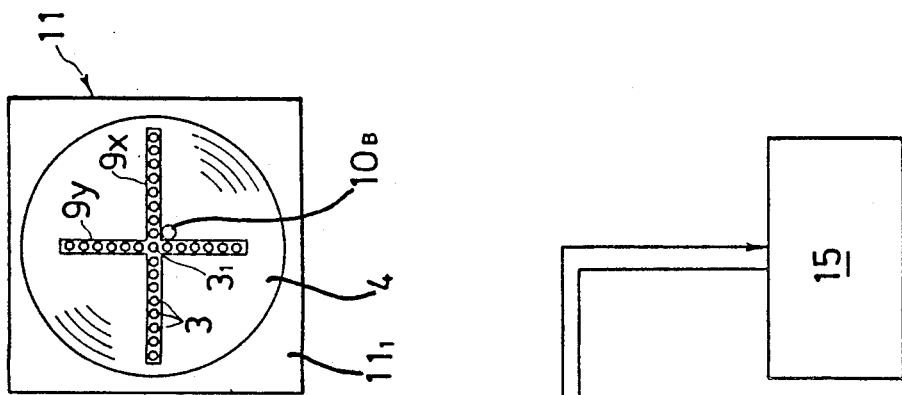
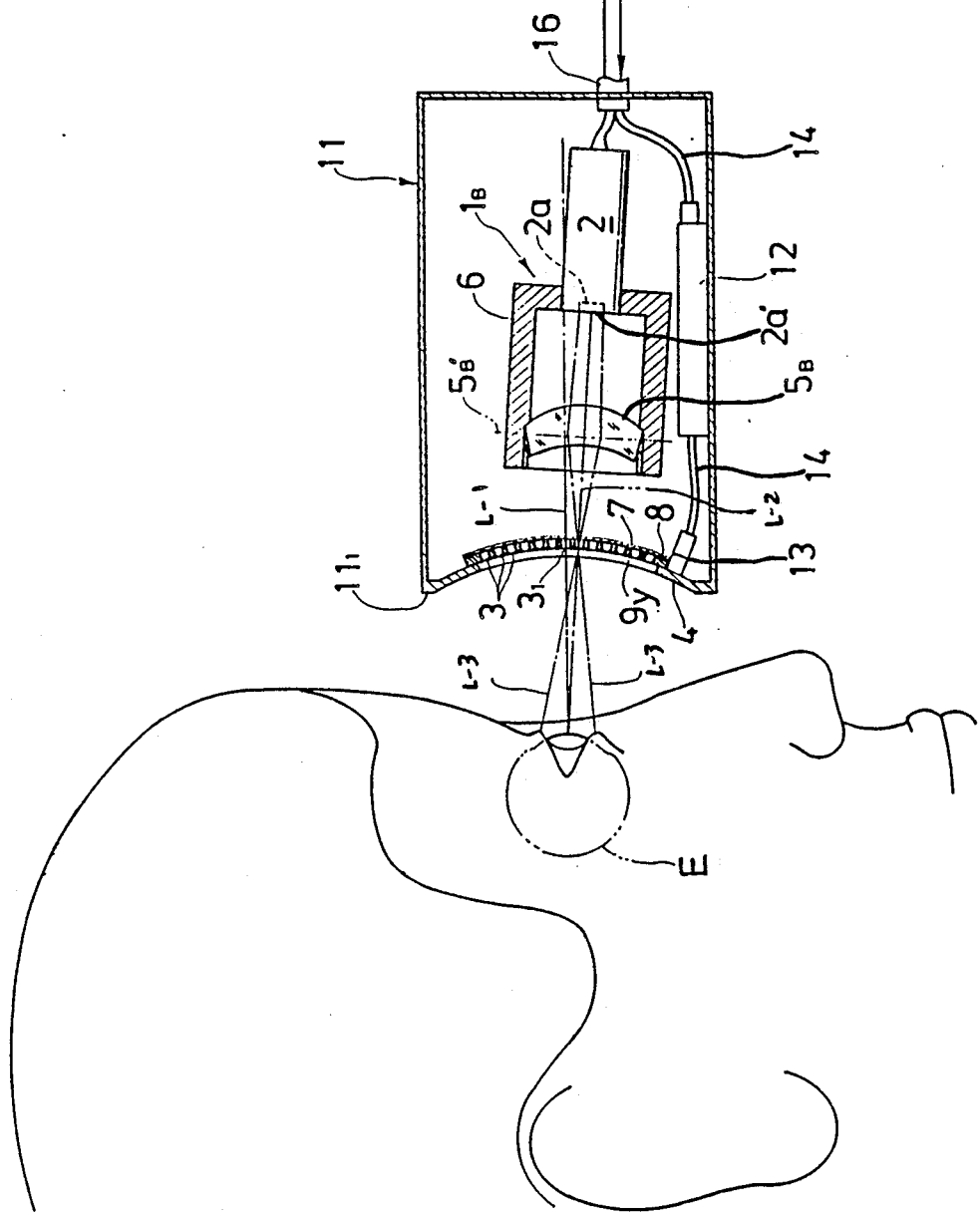

DEVICE FOR PHOTOGRAPHING EYE MOVEMENT

BACKGROUND OF THE INVENTION

1. Field of the Invention

The present invention relates to a device for photographing eye movement used for optical viewing in clinical diagnosis to observe, record and analyze an examinee's vertical, horizontal and rotational eye movement using a TV camera.

2. Prior Art

One of the most important diagnostic means used in clinical examination of an examinee's labyrinth, balance of nerves or functional disorders to the central nervous system is the measurement of eye movement. Since examination of a patient's eye movement can reveal symptoms of these problems, various eye movement testing devices are in use.

Commonly used devices such as an ENG, EOG and/or PENG include a polygraph device that records eye movement. Among devices used by the majority of medical practitioners is a device that directly observes eye movement using a 20-dioptry lens equipped with a light source which is called a Fresnel lens. Another device used is a search coil which uses a magnetic field to extract eye movement signals from a coil incorporated into a contact lens which is mounted on the examinee's eye.

However, EOG and PENG devices must be used in a darkened testing room with a separate target display and are problematic in that they cannot examine rotational eye movement. In addition, the Fresnel lens device cannot display targets and cannot record (and therefore analyze) the reactions of the eye movement. Furthermore, the search coil device cannot record a patient's natural eye movement.

In order to solve these problems found in the prior art, Japanese Patent Application No. 63-145425 was proposed by the inventors of the present application. The eye movement testing device of this Japanese application includes a pair of goggles that incorporate visible-ray source targets arranged horizontally and vertically in a cross shape. When used, the eyes are subjected to infrared rays, and the lighting of the targets is switched so that horizontal, vertical and rotational eye movement can be shot in a bright room with a TV camera. The examinee's eye movement image signals are then output from the TV camera for accurate observation, recording and analysis.

In this testing device, a plurality of targets are provided on a reflecting board which is of a prescribed shape so that the targets extend vertically and horizontally from the central target which is positioned on the axis of the eye. The optical axis of the TV camera is located proximately to the central target and penetrates the reflecting board. Accordingly, the image of the eye (the anterior part of the eye) on the light receiving element surface of the TV camera shows deviations both vertically and horizontally off the center of the pupil. Thus, measurement tends to be inaccurate.

Specifically as shown in FIG. 4, when the axis running through the center of the pupil of the anterior part C of the eye (which includes the cornea of the eyeball E) moves for the same angle in a direction A or B from the eye axis L-1, the eye axis L-1 runs through the central target of the cross-shaped target groups. However, the TV camera's optical axis L-2 running through the center of the pupil deviates for an angle α from the eye axis L-1 (shown on a single plane for the sake of explanation). Thus, though the image is formed on the image-forming surface 2a' of the light receiving element 2a positioned behind the shooting lens L and by the spherical-shaped anterior part of the eye Ca (with a circular front) shifted in the direction A from the eye axis L-1, such an image will be elliptical in shape and of a narrow width. If the image formed on the anterior part of the eye Cb, which is shifted in the direction B, the image will be elliptical in shape (Ib) and of a wider width, thus causing a difference in the widths of the images.

As can be seen from the above, even when the eye axis is moved (or shifted) an equal amount (distance) in either the A or B direction, deviation in the A direction will be smaller than deviation in the B direction on the image-forming surface of the light receiving element. However, since the resolution on the light receiving surface is constant at any position when the eye axis is shifted in the direction A (i.e., rotated away from the TV camera's optical axis), resolution deteriorates and measurement accuracy becomes lower compared to when the eye axis is shifted in the direction B.

SUMMARY OF THE INVENTION

It is the object of the present invention to solve the disadvantages found in the prior art and to provide a device for photographing eye movement which uses a target that allows photographing without lowering the resolution of the TV camera regardless of the direction of eye movement, thereby improving measurement accuracy.

In order to achieve this object, the device of the present invention uses a target group that consists of a plurality of visible-ray sources that are arranged vertically and horizontally, forming a cross-shaped target group with a central target positioned on the eye axis of the examinee, and the turning on and off of a target which comprises LED lights (target group) is controlled by a light controlling means. In addition, a TV camera is provided so that at least a principal point of the lens of the TV camera is located at a prescribed position on a line that passes near the central target of the target group and goes towards the center of the examinee's pupil. The center of a light receiving surface of a light receiving element is located on the above mentioned line (which passes near the central target) and the light receiving surface crosses perpendicular to the eye axis so that an image of the eye is formed on the light receiving surface.

In such a structure it is effective to arrange the principal plane of the lens which passes through its principal point so that it crosses perpendicular to the eye axis.

It is also effective to arrange each target so that its light-emitting part is on a spherical surface that extends around the center of rotation of the eye.

The object of the present invention can be accomplished by another structure which uses the same type of target group as described above. However, in this second device, the front aperture of the lens of the TV camera is set on a line passing near the central target and running toward the center of the examinee's pupil on a surface where the targets are provided. The TV camera equipped with the front-aperture lens is provided behind the target group so that the light axis of the camera is positioned on the line running in the direction of the center of the examinee's pupil, thereby allowing the image of the eye (anterior part of the eye) to be formed on the light receiving surface of the light receiving element.

As in the first device described above, it is preferable to arrange each target of the target group so that its light-emitting part is on the spherical surface that extends around the center of rotation of the eye.

In both devices, the principal point of the lens of the TV camera is located on the line running towards the center of the examinee's pupil, and the TV camera is provided so that the center of the light receiving surface thereof is positioned on such line and the light receiving surface crosses perpendicular to the eye axis that runs through the central target of the target group so that an image of the eye (an image of the anterior part of the eye) is formed on the light receiving surface. Thus, due to the so-called shift-shooting principle, eye movement is photographed so that an image which is not distorted in both the X and Y directions (vertically and horizontally) around the axis of the eye (i.e., around the center of the pupil when the examinee is looking straight ahead) can be formed, increasing measurement accuracy significantly.

In this case, since the principal plane of the lens is set perpendicular to the eye axis, (i.e., parallel to the light receiving surface), the aperture of the lens does not need to be narrowed so much, meaning that a good image can be obtained with a large effective diameter.

In addition, since the optical axis of the lens is matched to the line running toward the center of the pupil, more uniform light is obtained in the surrounding area. In order to get a sharper image in the surrounding area, the aperture has to be narrowed.

Since the target group is set so that the light-emitting part thereof is provided on a spherical surface centered around the rotational center of the eye, corrections based upon the position of the target become unnecessary when measuring the image of eye movement.

The front aperture of the lens of the TV camera is positioned at the intersection of the line running toward the center of the examinee's pupil and the plane formed by the target group, and the TV camera having a front-aperture type lens behind the target group is provided so that its optical axis is positioned on the line running toward the center of the pupil, so that an image of the eye (an image of the anterior part of the eye) is formed on the light receiving surface. Thus, since the image-forming optical path converges and becomes thin where it passes through the plane on which the target group is formed, the optical axis of the TV camera can be installed near the center of the target group and as close as possible to the eye axis so that the optical axis of the TV camera becomes quasi-identical to the eye axis. As a result, distortion of the image formed on the light receiving surface can be as small as possible so as to take advantage of the resolution of the TV camera and to improve measurement accuracy.

Furthermore, since the light-emitting part of the target is placed on the spherical plane centered around the rotational center of the eye, correction depending upon the position of the target will no longer be necessary during measurement of eye movement.

BRIEF DESCRIPTION OF THE DRAWINGS

FIG. 5 is a vertical sectional view of the main part of the device of a second embodiment of the present invention when eye movement is being photographed;

FIG. 7 is a front view thereof viewed from the examinee side.

DETAILED DESCRIPTION OF THE INVENTION

The present invention will now be explained with reference to the accompanying drawings.

Figure 1:
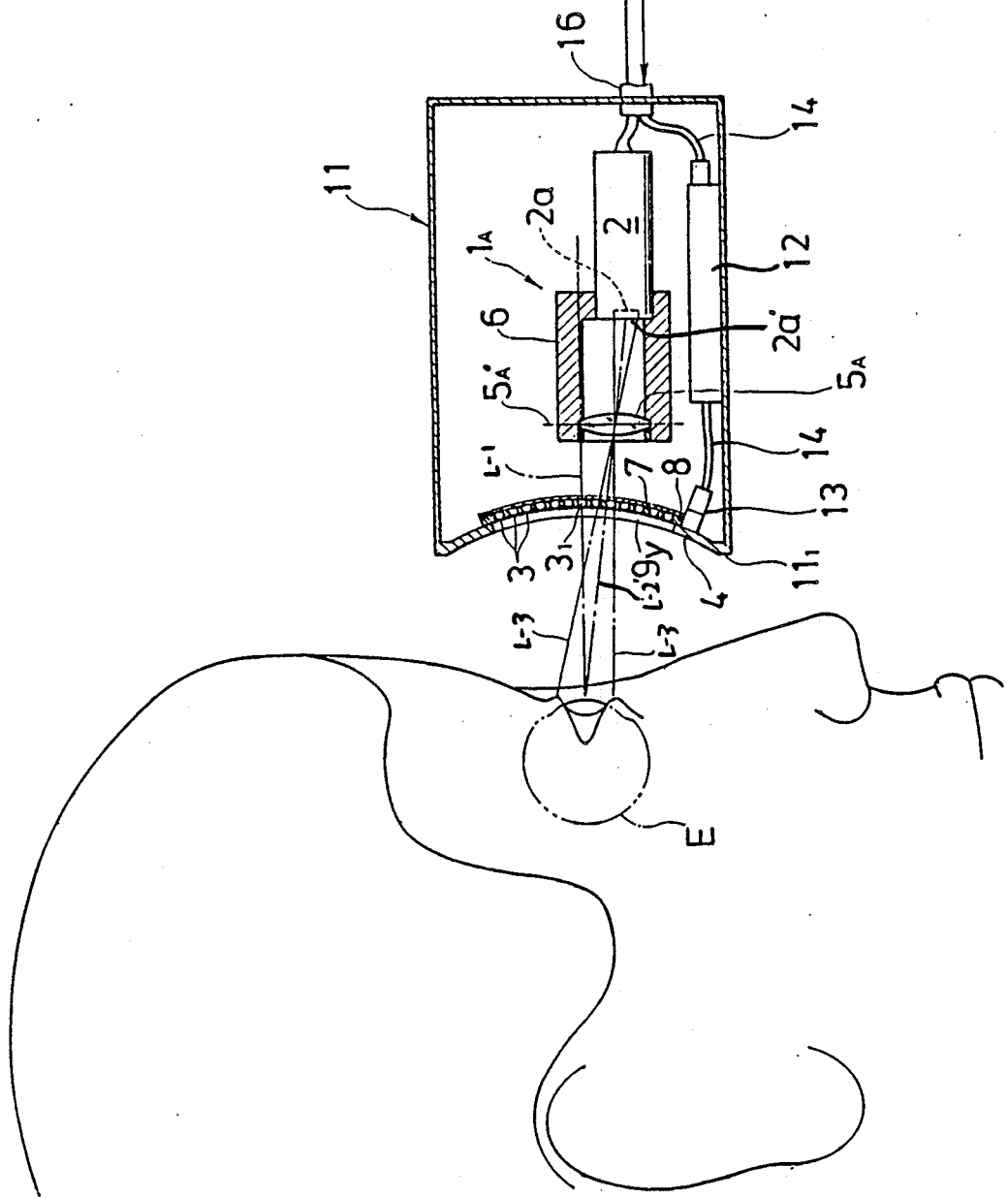
FIG. 1 is a vertical sectional view of the main part of the device of a first embodiment of the present invention when the eye movement is being photographed.
Figure 2:
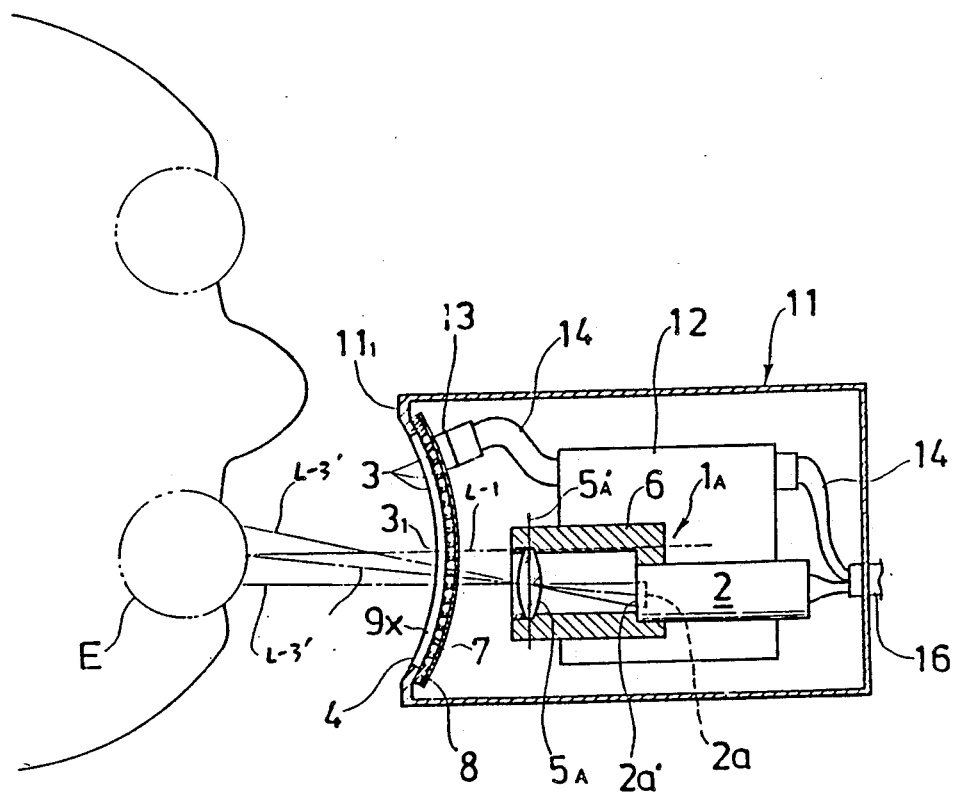
FIG. 2 is a horizontal sectional view thereof.

FIGS. 1 and 2 show a first embodiment of the present invention.

The device of this invention comprises a subminiature TV camera 1A for photographing eye movement and a group of target (comprising LED lights) provided in front of the camera. The targets (described in detail later) are designed to be "movable". In other words, the targets look like they are moving as a result of being turned on and off so that the examinee can follow the lighted target.

A reflector 4 is a spherical shape which encompasses the circle circled around the center of an examinee's eye movement. A coating or painting is applied to its surface. The reflector 4 is provided on the front end of a casing 11 that contains the TV camera 1A. A cross-shaped window comprising window openings 9x and 9y are provided so that the light from the targets can pass therethrough in both horizontal (9x) and vertical (9y) directions.

A certain number of LEDs 3 are arranged in a cross-shape and provided behind the window openings 9x and 9y to form a target group. The cross-shaped target group has a central target LED 3-1 in the middle, and other LEDs are positioned horizontally and vertically at prescribed intervals. The target group is attached on a flexible board 7 via a supporting part 8 by bonding or other means. Each target LED (target light) 3 on the flexible board 7 can be lit when electrical continuity is established between the LEDs and a connector 13 which is provided behind the reflector 4. Lighting (on and off) of the target LEDs is controlled by the connector 13 which is connected to a target controller 12 via a flexible cord 14. The target controller 12 is installed in the casing 11 and activated by a control signal from an analyzer 15 provided outside the casing 11.

Figure 3:
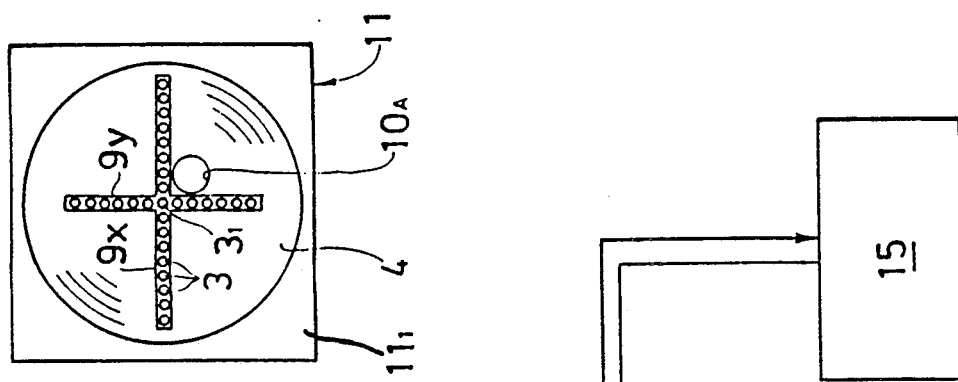
FIG. 3 is a front view thereof viewed from the examinee side.

As shown in FIG. 3, a through window 10A with a predetermined diameter is opened on the reflector 4 so that it is aligned to the light path of the image of the eye and is positioned near the central target LED 3-1 at the center or the intersecting point of the cross-shaped target LEDs. The window 10A can be formed so that it is square in shape, with its edges(s) contacting the cross-shaped window openings 9x and 9y.

The TV camera 1A is provided behind the window 10A. The camera 1A is provided on the light path of the eye image and has a subminiature TV (pick-up tube) 2. The TV 2 has a shooting lens 5A and light receiving elements 2a (such as C, C and D) at the front end. The light receiving surface 2a' of the light receiving element 2a of the TV camera IA is parallel to the principal plane 5A' of the lens 5 that passes through a principal point of the lens 5A. The principal plane 5A' of the lens 5A and the light receiving surface 2a' are positioned to perpendicularly cross the eye axis L-1, and the center of the pupil is positioned on the line L-2' that connects the principal point of the lens 5A d the center of the light receiving element surface 2a'. Thus, the light receiving element 2a is in the front lower part of a shooting lens supporting pipe 6, so that the center of the light receiving surface 2a' is off the optical axis (not shown) of the lens 5. In other words, the center of the light receiving surface 2a' is positioned in a diagonal position in the front lower part of the optical axis (not shown) of the lens 5.

The TV camera 1A is placed at a prescribed position so that the principal plane 5A' of the shooting lens 5A and the light receiving surface 2a' perpendicularly cross the optical axis L-1 that passes through the central target 3-1.

Thus, when the eye image is formed on a light receiving surface 2a', the optical path of the eye is not interrupted by the window 10A of the reflector 4 (or a flexible board mounting part, if necessary), and the image can be formed on the light receiving surface 2a' without any deformation.

In FIG. 1, lines L-3 represent principal optical paths which come from the top and bottom edges of the eye (anterior part of the eye) and pass through the principal point of the lens 5A to form an image on the light receiving surface 2a'.

In FIG. 2, lines L-3' represent principal optical paths which come from the right and left edges of the eye (the anterior part of the eye) and pass through the principal point of the lens 5A to form an image on the light receiving surface 2a'.

The window 10A is formed on the reflector 4 so as to correspond to the required valid diameter of the lens. Since the flux of the light that passes through the reflector 4 has a predetermined width, its principal optical path L-2' is substantially tilted from the eye axis L-1 even when it is positioned close to the eye axis. However, since both the shooting lens 5A and the light receiving surface 2a' are provided so that they have a shift effect, an eye image which is free of any deformation can be formed on the light receiving surface 2a'.

When an examination is performed, the lighting (on and off) of the target LEDs 3 of the cross-shaped target group is controlled by control signals emitted from the analyzer 15 via the target controller 12. By turning the LEDs on and off, the lit spots move (or look as if they are moving) vertically and horizontally to optically stimulate the examinee's eye. The examinee's eye movement which follows these lit target LEDs is photographed by the pick-up tube 2 of the TV camera 1A which is driven by synchronizing signals from the analyzer 15 and is then sent to an image processing section of the analyzer 15 again as an image signal, properly processed, projected on a TV screen, and then visually examined, after which the necessary examination results are recorded in a recording device.

In this case, since the image formed on the light receiving surface 2a' is not deformed, and it is possible to analyze the examination by making the utmost of the resolution of the TV camera uniformly on each part of the reproduced image, extremely accurate measurement results can be obtained.

In the Figures for the first embodiment as well a the second embodiment described below, the target group is shown as a sectional view on the eye axis of the examinee, and the TV camera is shown in a sectional view taken along a line passing through the principal point of the lens and the light receiving element for explanatory purposes.

A second embodiment of the present invention will now be given with reference to FIG. 5 which shows a vertical sectional view of a principal section of the device and FIG. 6 which shows a plan view thereof.

The feature of the second embodiment is that the optical axis of the TV camera is positioned as close to the eye axis as possible to make the optical axis of the TV camera quasi-identical to the eye axis.

Specifically, the shooting device is provided with a reflector 4 which is the same as the one used in the first embodiment (except the reflector of the second embodiment has a round window on the optical path of the eye image) in front of a subminiature TV camera 1B. The target LEDs are also the same as in the first embodiment.

As seen in FIG. 7, a window 10B which is smaller in diameter than the window 10A of the first embodiment is formed on the reflector 4 and on the optical path of the eye image. The window 10B is closer to the central target LED 3-1 than the window 10A of the first embodiment is. As described in the first embodiment, the window 10B can be formed in a square which contacts the intersecting point and is adjacent to the cross-shaped window openings 9x and 9y.

In the first embodiment, a regular shooting lens is used. In the second embodiment, a front-aperture type shooting lens 5B is used so that the front-aperture is flush to a plane on which the light-emitting parts of the targets group are formed. The TV camera IB is positioned so that the front-aperture position, where the narrow band of gathered light of the optical path of the eye comes into the camera, is not interrupted by the target group so that optical axis L-2 is set as close as possible to the optical path of L-1 of the eye.

In FIG. 5, lines L-3 and L-3 represent the principal optical paths from the top and bottom edges of the eye (the anterior part) passing through the front-aperture part of the lens 5B and refracted by the lens 5B (that is imaginary refraction on the principal plane 5B') to form an image on the light receiving surface 2a'.

Figure 6:
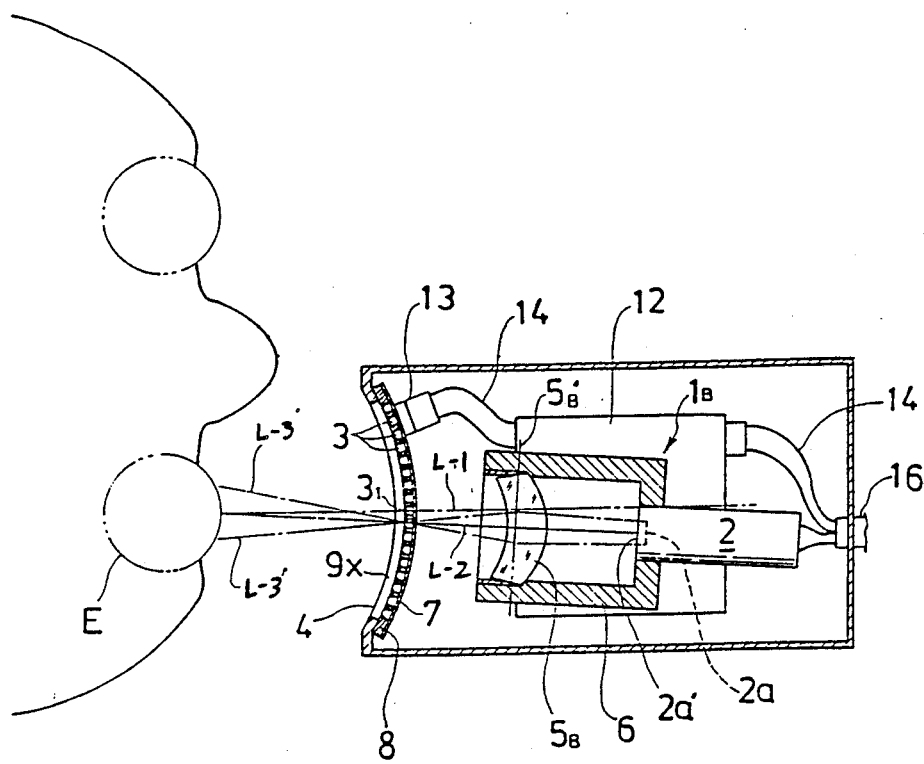
FIG. 6 is a sectional top plan view thereof.
Figure 4:
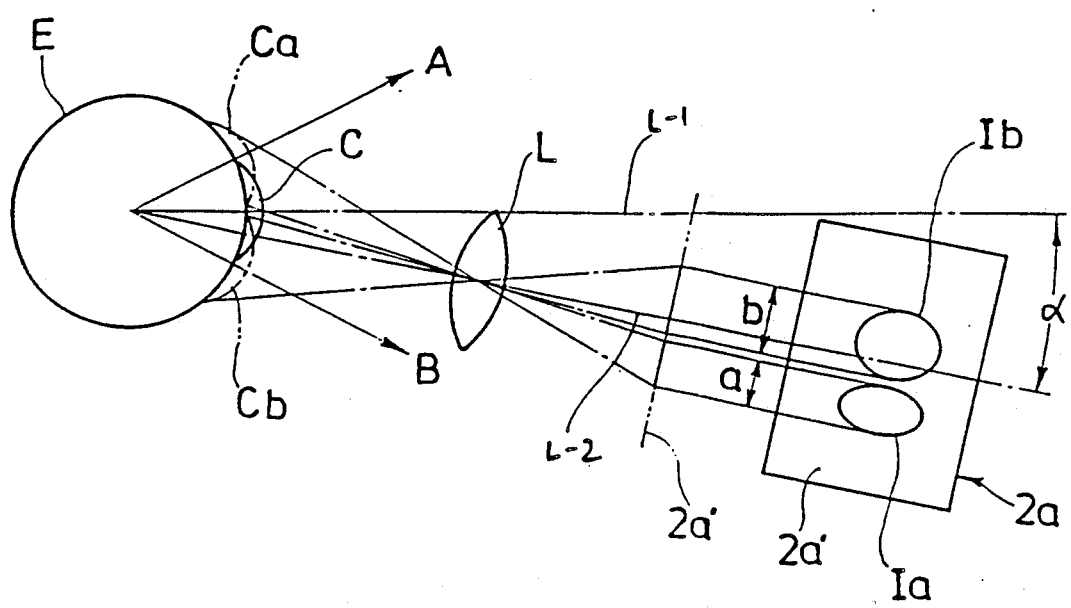
FIG. 4 is a simulated view showing an eye (anterior part of the eye) image formed on the light receiving element surface of the conventional eye movement photographing device.

Lines L-3' and L-3' in FIG. 6 represent principal optical paths from the right and left edges of the eye (the anterior part) passing through the front-aperture part of the lens 5B and then refracted by the lens 5B to form an image on the light receiving surface 2a'.

As illustrated in FIGS. 5 and 6, the principal optical path intersects at the front-aperture position. Thus, the window 10B can be of a smaller diameter so that a narrow band of light which matches the valid diameter of the shooting lens of the reflector 4 can pass through.

As described above, by setting the optical axis L-2 of the shooting lens 5B to be quasi-identical to the eye-axis L-1 which passes the central LED 3-1 of the cross-shaped target LEDs, deviation of the image of eye movement formed on the light receiving surface 2a' decreases substantially, and the analyzing function of the TV camera is fully utilized to improve measurement accuracy.

In order to avoid complex illustration of the optical path required to form an image on the eye, only the principal optical path of the essential part of the eye is shown in the drawings.

Since the target LEDs are placed on the spherical surface centered around the movement of the eye in both the first and second embodiments, no adjustment of the position of the targets is required during examination.

In the above described two embodiments, examination can be performed effectively in a bright room so that room light can be used along with the reflector to photograph eye movement. However, it is also possible to use the device in a pair of goggles which make a dark area in front of the examinee's eyes. In this case, it is recommended to place an infrared light source, such as an infrared-ray light-emitting-diode IP-LED on both sides of the front part of the reflector to illuminate the reflector. It is further recommended to use an infrared-ray sensor TV camera and to control the lighting of the targets and examine the examinee's eye movement in such a way that the eye movement is not fixed, but kept free so that effective observation, recording and measurement can be achieved.

In the eye movement shooting device of the first embodiment, the principal point of the lens of the TV camera is located on a line passing near the central target of the cross shaped target group and running towards the center of the examinee's pupil, and the center of the light receiving surface of the light receiving element is located on such line so that the light receiving surface is perpendicular to the eye axis. Therefore, in accordance with the so-called principle of shift-shooting, an undistorted image of eye movement can be obtained for measurement of various parts of the image using the TV camera's resolution most effectively, thereby making accurate observation of eye movement and high-precision measurement possible.

In addition, since the principal plane of the shooting lens of the TV camera crosses the eye axis perpendicularly, the aperture of the lens is narrowed to a smaller degree, making it possible to obtain a good image with a large effective diameter for efficient measurement.

Furthermore, the light-emitting part of the target is arranged on a spherical surface centered around the rotational center of the eye; therefore adjustment or correction of the target position will not be necessary when measuring the eye movement image.

In the eye movement shooting device of the second embodiment, the front-aperture of the lens of the TV camera is provided on the plane where the target group is provided. Thus, the eye axis passing through the central target of the target group and the optical axis of the TV-camera are brought as close together as possible to minimize distortion of the image formed on the light receiving surface of the light receiving element in order to effectively use the TV camera resolution and to improve measurement precision of the image.

Furthermore, in the second embodiment it is not necessary to make corrections according to the target position when measuring eye movement images.

We claim:

1. A device for photographing eye movement comprising:
    a target group consisting of a plurality of light emitting targets which are arranged vertically and horizontally from a central target positioned on the eye axis of an examinee to form a cross-shaped target, lighting of said light emitting targets of said target group being controlled by a lighting control means;
    a TV camera positioned at a predetermined position being said target group such that at least a front aperture of a shooting lens of said TV camera is located at a prescribed position on a line that passes near said central target and going towards the center of said examinee's pupil; and
    a light receiving element having a light receiving surface located on said line so that said light receiving surface is perpendicular to said eye axis and an eye image is formed on said light receiving surface.

2. A device according to claim 1, wherein said shooting lens of said TV camera is positioned such that a principal plane thereof which passes a principal point of said lens crosses perpendicular to said eye axis.

3. A device according to claim 1 or 2, wherein a light emitting means used as a target of said target group is positioned on a spherical surface centered around the rotational center of an eye.

4. An eye movement shooting device comprising:
    a target group consisting of a plurality of light emitting elements that are arranged vertically and horizontally from a central target positioned on the eye axis of an examinee to form a cross-shaped target, lighting of said light emitting elements of said target group being controlled by a lighting control means;
    a TV camera provided at a predetermined position behind said target group so that a front-aperture of a shooting lens of said camera is positioned on a line which passes near said central target and advances towards an examinee's pupil and on a plane on which said target group is provided, the optical axis of said TV camera being positioned on said line so that an eye image is formed on a light receiving surface of said TV camera.

5. A device according to claim 4, wherein a light emitting part used as a target of said target group is provided on a spherical surface centered around the rotational center of an eye.

6. A device for photographing eye movement comprising:
    a casing provided with a reflector at the front end, said reflector being curved so as to make the same spherical surface as the rotational center of the eye and provided with a cross-shaped opening and a through hole next to said cross-shaped opening;
    a target group installed in said casing, said target group consisting of a plurality of light emitting elements arranged in a cross-shape so that light from said target group can pass through said cross-shaped opening of said reflector, a light source at the center of said target group being aligned on the eye axis of an examinee;
    a photographing means installed in said casing and behind said target group, said photographing means being positioned so that a center of a lens and a center of a light receiving surface of said photographing means and said through hole on said reflector is aligned on a line from the center of an examinee's pupil.

* * * * *